United States Patent
Johnston et al.

(10) Patent No.: US 9,913,695 B2
(45) Date of Patent: Mar. 13, 2018

(54) ROBOTIC SYSTEM INCLUDING A CABLE INTERFACE ASSEMBLY

(71) Applicant: MEDROBOTICS CORPORATION, Raynham, MA (US)

(72) Inventors: Gabriel Johnston, Raynham, MA (US); Tom Calef, Bridgewater, NJ (US); Ian Darisse, Brighton, MA (US); Brett Zubiate, Duxbury, MA (US); R. Maxwell Flaherty, Auburndale, FL (US); J. Christopher Flaherty, Auburndale, FL (US); Reynaldo Lewis, New Bedford, MA (US); Adam Rienzie, Brockton, MA (US); Justin S. Runyon, Buzzards Bay, MA (US); Anthony Ray Halloway, Jr., Boston, MA (US); Corey Anthony Malaquais, Ludlow, MA (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 14/888,189

(22) PCT Filed: May 2, 2014

(86) PCT No.: PCT/US2014/036571
§ 371 (c)(1),
(2) Date: Oct. 30, 2015

(87) PCT Pub. No.: WO2014/179683
PCT Pub. Date: Nov. 6, 2014

(65) Prior Publication Data
US 2016/0067000 A1    Mar. 10, 2016

(51) Int. Cl.
*A61B 1/005*    (2006.01)
*A61B 1/01*    (2006.01)
(Continued)

(52) U.S. Cl.
CPC .............. *A61B 34/30* (2016.02); *A61B 34/71* (2016.02); *A61B 2034/301* (2016.02)

(58) Field of Classification Search
CPC . B25J 9/0015; B25J 9/065; B25J 9/104; B25J 9/1045; B25J 9/1075
(Continued)

(56) References Cited

U.S. PATENT DOCUMENTS 3,060,972 A    10/1962    Sheldon
3,557,780 A     1/1971    Sato
(Continued)

FOREIGN PATENT DOCUMENTS

EP    0653922    11/2005
EP    1015068     9/2011
(Continued)

OTHER PUBLICATIONS

Expo-70 Robot—Vadim Matskevich's students, http://cyberneticzoo.com/wp-content/uploads/2010/03/Expo-70-MK-1969-02-p31-3.pdf, 1969.
(Continued)

*Primary Examiner* — William Kelleher
*Assistant Examiner* — Bobby Rushing, Jr.
(74) *Attorney, Agent, or Firm* — Onello & Mello, LLP

(57) ABSTRACT

A system and method for performing a medical procedure includes a first multi-linked mechanism comprising a plurality of first links, and a lumen therethrough; a second multi-linked mechanism comprising a plurality of second links, wherein the second multi-linked mechanism is constructed and arranged to be slidingly received by the lumen of the first multi-linked mechanism, and where the first and second multi-linked mechanisms are configured to transition from a limp state to a rigid state; a set of proximal cables comprising at least a first proximal cable and a second
(Continued)

proximal cable; a set of distal cables comprising at least a first distal cable and a second distal cable; a cable control assembly constructed and arranged to independently apply tension to the first proximal cable and the second proximal cable; a cable interface assembly constructed and arranged to receive a force from at least the first proximal cable and the second proximal cable and to transmit a corresponding force to at least the first distal cable and the second distal cable. The force applied to the first distal cable and the second distal cable steers at least one of the first multi-linked mechanism or the second multi-linked mechanism.

33 Claims, 7 Drawing Sheets

(51) Int. Cl.
*A61B 34/30* (2016.01)
*A61B 34/00* (2016.01)

(58) Field of Classification Search
USPC .................................. 901/21; 600/146, 528
See application file for complete search history.

(56) References Cited

U.S. PATENT DOCUMENTS

| | | | |
|---|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hlll |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A * | 4/1987 | Iwashita ............... A61B 1/0052 138/120 |
| 4,661,032 A | 4/1987 | Arai |
| 4,666,366 A | 5/1987 | Davis |
| 4,700,693 A * | 10/1987 | Lia ....................... A61B 1/0055 356/241.4 |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,919,112 A * | 4/1990 | Siegmund .......... A61B 1/00105 600/136 |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,193,963 A | 3/1993 | McAffee et al. |
| 5,195,968 A | 4/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 10/1995 | Heckele |
| 5,524,180 A | 6/1996 | Wang et al. |
| 5,759,151 A | 6/1998 | Sturges |
| 5,815,640 A | 9/1998 | Wang et al. |
| 5,841,950 A | 11/1998 | Wang et al. |
| 5,907,664 A | 5/1999 | Wang et al. |
| 6,080,181 A | 6/2000 | Jensen et al. |
| 6,132,368 A | 10/2000 | Cooper |
| 6,346,072 B1 | 2/2002 | Cooper |
| 6,817,974 B2 * | 11/2004 | Cooper ............ A61B 17/00234 600/142 |
| 6,837,846 B2 | 1/2005 | Jaffe et al. |
| 6,837,847 B2 | 1/2005 | Ewers et al. |
| 7,357,774 B2 | 4/2008 | Cooper |
| 7,789,875 B2 | 9/2010 | Brock et al. |
| 7,819,885 B2 | 10/2010 | Cooper |
| 7,850,642 B2 | 12/2010 | Moll et al. |
| 7,854,109 B2 | 12/2010 | Zubiate et al. |
| 7,854,738 B2 * | 12/2010 | Lee ..................... A61B 34/20 606/130 |
| 7,867,241 B2 * | 1/2011 | Brock .................. A61B 34/20 600/114 |
| 7,946,546 B2 | 5/2011 | Zubiate et al. |
| 8,100,031 B2 | 1/2012 | Zubiate et al. |
| 8,192,422 B2 | 6/2012 | Zubiate et al. |
| 8,257,303 B2 * | 9/2012 | Moll ..................... A61B 34/20 600/114 |
| 8,459,138 B2 | 6/2013 | Zubiate et al. |

(56) References Cited

U.S. PATENT DOCUMENTS

| | | | |
|---|---|---|---|
| 8,518,024 B2* | 8/2013 | Williams | A61B 1/0052 606/1 |
| 8,603,077 B2* | 12/2013 | Cooper | G05G 9/00 606/1 |
| 8,992,421 B2 | 3/2015 | Stand et al. | |
| 2002/0091374 A1 | 7/2002 | Cooper | |
| 2004/0138529 A1 | 7/2004 | Wiltshire et al. | |
| 2005/0021050 A1 | 1/2005 | Cooper | |
| 2005/0216033 A1 | 9/2005 | Lee et al. | |
| 2006/0199999 A1 | 9/2006 | Ikeda et al. | |
| 2008/0147091 A1 | 6/2008 | Cooper | |
| 2008/0245173 A1 | 10/2008 | Schwerin et al. | |
| 2009/0171151 A1 | 7/2009 | Choset et al. | |
| 2010/0160735 A1 | 6/2010 | Bakos | |
| 2011/0028990 A1 | 2/2011 | Cooper | |
| 2011/0056320 A1 | 3/2011 | Zubiate et al. | |
| 2011/0066161 A1 | 3/2011 | Cooper | |
| 2011/0118707 A1* | 5/2011 | Burbank | A61B 34/30 606/1 |
| 2011/0152613 A1 | 6/2011 | Zubiate et al. | |
| 2011/0152878 A1* | 6/2011 | Trusty | A61B 1/00133 606/130 |
| 2011/0184241 A1 | 7/2011 | Zubiate et al. | |
| 2011/0313243 A1 | 12/2011 | Zubiate et al. | |
| 2014/0012287 A1 | 1/2014 | Oyola et al. | |
| 2014/0371764 A1 | 12/2014 | Oyola et al. | |
| 2015/0313449 A1 | 11/2015 | Stand et al. | |

FOREIGN PATENT DOCUMENTS

| | | |
|---|---|---|
| WO | 2012015659 | 2/2012 |
| WO | 2012054829 | 4/2012 |
| WO | 2013039999 | 3/2013 |

OTHER PUBLICATIONS

Conductor Robot, http://cyberneticzoo.com/wp-content/uploads/2010/03/Ticket-robot-russian-1973.pdf, 1973.
Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.
Lee E. Weiss, Arthur C. Sanderson, Charles P. Neuman, "Dynamic Sensor Based Control of Robots with Visual Feedback", IEEE Journal of Robotics and Automation, 1987, p. 404-417.
Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.
Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.
Xu Hongbin, "Stability and performance robustness analysis of hybrid control for robot manipulators", Journal of UEST of China, vol. 22 No. 5, Oct. 1993, p. 501-505.
Francois Chaumette, Patrick Rives, Bernard Espiau, "Positioning of a Robot With Respect to an Object, Tracking It and Estimating Its Velocity by Visual Servoing", IEEE International Conf. on Robotics and Automation, 1991, p. 2248-2253.
A.V. Timofejev, N.V. Ivanova, "Expert System of the Control Programs Designing of Adaptive Robots", The Lenigrand Institute of Aircraft Instrumentation, 1991, p. 912-915.
W Szczepiński, "Theory of polyhedrons of positioning accuracy of manipulators", Mechanism and Machine Theory; Institute of Fundamental Technological Research , Polish Academy of Sciences, 00-049 Warsaw, Swietokrzyska 21, Poland, 1991, p. 697-709.
Junji Furusho, Hiroshi Nagao, Naruse Makoto, "Multivariable Root Loci of Control Systems of Robot Manipulators with Flexible Driving Systems : Distortion Feedback ", JSME International Journal, 1992, p. 65-73.
Potemkin, E., Astafurov, P., Osipov, A., Malenkov, M., Mishkinyuk, V., Sologub, P., "Remote-controlled robots for repair and recovery in the zones of high radiation levels ", Robotics and Automation, IEEE, 1992, p. 80-82.
S. L. Shishkin, "Adaptive control of a biped robot walking across a horizontal plane", International Journal of Adaptive Control and Signal Processing, 1992, p. 259-264.
Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.
Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.
J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.
Timopheev, A.V., Prokhorov, D.V., "Neural networks processing systems in recognition and control problems", Neuroinformatics and Neurocomputers; IEEE, 1992, p. 820-828.
Jianguo Fu, Naresh K. Sinha, "An iterative learning scheme for motion control of robots using neural networks: A case study", Journal of Intelligent & Robotic Systems, 1993, p. 375-398.
Troccaz, J. Lavallee, S. Hellion, E., "A passive arm with dynamic constraints: a solution to safety problems in medical robotics", Systems Engineering in the Service of Humans, Conference Proceedings, 1993, p. 166-171.
Swarup, M. Gopal, "Comparative study on linearized robot models", Journal of Intelligent & Robotic Systems, 1993, p. 287-300.
H. Azaria, A. Dvir, "Algorithm optimization using a rule-based system. A case study: The Direct Kinematic Solution in robotics", Journal of Intelligent & Robotic Systems, 1993, p. 309-324.
Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.
K. Periyasamy, V. S. Alagar, T. D. Bui, "A formal framework for design and verification of robotic agents", Journal of Intelligent & Robotic Systems, 1993, p. 173-200.
S. Nicosia, A. Tornambè, P. Valigi, "State estimation in robotic manipulators: Some experimental results", Journal of Intelligent & Robotic Systems,, 1993, p. 321-351.
Dimitrios M. Emiris, Vassilios D. Tourassis, "Singularity-robust decoupled control of dual-elbow manipulators", Journal of Intelligent & Robotic Systems, 1993, p. 225-243.
M.M. Bayoumi, "Adaptive Control of Robots with Rigid Links: A Status Report", Department of Electrical Engineering, Queen's University, Ontario, Canada (IEEE), 1993, p. 232-236.
Y. Edan, B. A. Engel, G. E. Miles, "Intelligent control system simulation of an agricultural robot", Journal of Intelligent & Robotic Systems, 1993, p. 267-284.
Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.
Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.
E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.

(56) References Cited

OTHER PUBLICATIONS

A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.
E. V. Panteley, A. A. Stotsky, "Adaptive trajectory/force control scheme for constrained robot manipulators", International Journal of Adaptive Control and Signal Processing, 1993, p. 489-496.
Filaretov, V.F., "A Synthesis of Adaptive Control Systems for Industrial Robots ", Electronic Mfg Technology Symposium, 1993, p. 168-171.
S. Zenkevich, A. Maximov, A. Nazarova, A. Korshunov, "Control of robot-based assembly cell ", Lecture Notes in Control and Information Sciences , 1993, p. 418-477.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Part 1 Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.
Jacobsen, S.C., Iversen, E.K., Knuth, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with a Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.

(56) References Cited

OTHER PUBLICATIONS

Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a Hybrid Virtual-Real Structure, RoManSy 9: Proceedings of the Ninth CISM-IFToMM Symposium on Theory and Practice of Robots and.
James K. Mills, Hybrid Actuator for Robot Manipulators: Design, Controland Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A. , Model of Foveal Visual Preprocessor, Intelligent Robots and Computer Vision XIV: Algorithms, Techniques, Active Vision, and Materials Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
ZH Luo , "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTA Automatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.

Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K. Rist, Ellen Y. Lin, Bartholomew O. Nnaji, Ralph Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-Axes Scara Robot, Journal of the Japan Society of Precision Engineering , 1993, p. 423-428.
H.S. Moon, S.Y. Lee, S.J. Na, a Study on Selection of Gas Metalarc Welding Parameters of Fillet Joints Using Neural Network, Journal of the Korean Welding Society, 1993, p. 151-160.
Byong Suk Kim, Computer-Assisted System for Accident Analysis and Mul-Function Protection in Industrial Robot, Papersearch.net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim) , Safe Speed Limit of Robot Arm During Teaching and Maintenance Work, 1993, p. 64-70.
Chang-Boo Kim, Seung-Hoon Lee, Inverse Dynamic Analysis of a Flexible Robotarm With Multiple Joints by Using the Optimal Control Method, Journal of the Korean Society of Precision Engineering , 1993, p. 133-140.
Chang-Soo Han, The Optimum Design of a 6 D.O.F. Fully-Parallel Micromanipulator for Enhanced Robot Accuracy, Journal of the Korean Society of Precision Engineering , 1993, p. 42-51.
Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robotand Cnc Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering , 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development Ofa Robot Wrist for the Assembly of Chamferless Parts, Journal of the Korean Society of Precision Engineering , 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries Ltd, 1992, p. 233-238.
Jin-Geol Kim, A Study on the Robust Digital Tracking Control of a Robot With Flexible Joints, Journal of the Korean Society of Precision Engineering , 1992, p. 92-100.

(56) References Cited

OTHER PUBLICATIONS

Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot's Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering , 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joon Choi, Ki-Sang Hong, Hong Joeng, The Development of Intelligent Robot Using Vision and Speech Recognition System, Department of EE, Postech, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering , 1993, p. 170-177.
A Study on a Basic System Configuration for the PC Interface and the Robot Trajectory Generation, 1993, p. 354-358.
G.T. Yang, S.D. Ahn, S.C. Lee, Tip Position Control of Flexible Robotarm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
ASEA Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
L.E. Weiss, "Dynamic Visual Servo Control of Robots: an adaptive image-based approach, Technical Report", Part 2 Carnegie Mellon, 1984.
L.E. Weiss, "Dynamic Visual Servo Control of Robots: an adaptive image-based approach, Technical Report", Part 3 Carnegie Mellon, 1984.
ISRWO dated Mar. 11, 2015.
Extended European Search Report dated Dec. 19, 2016 issued in corresponding European Application No. 14791655.5.
Australian Office Action dated Sep. 21, 2017 issued in corresponding Australian Application No. 2014259679.

\* cited by examiner

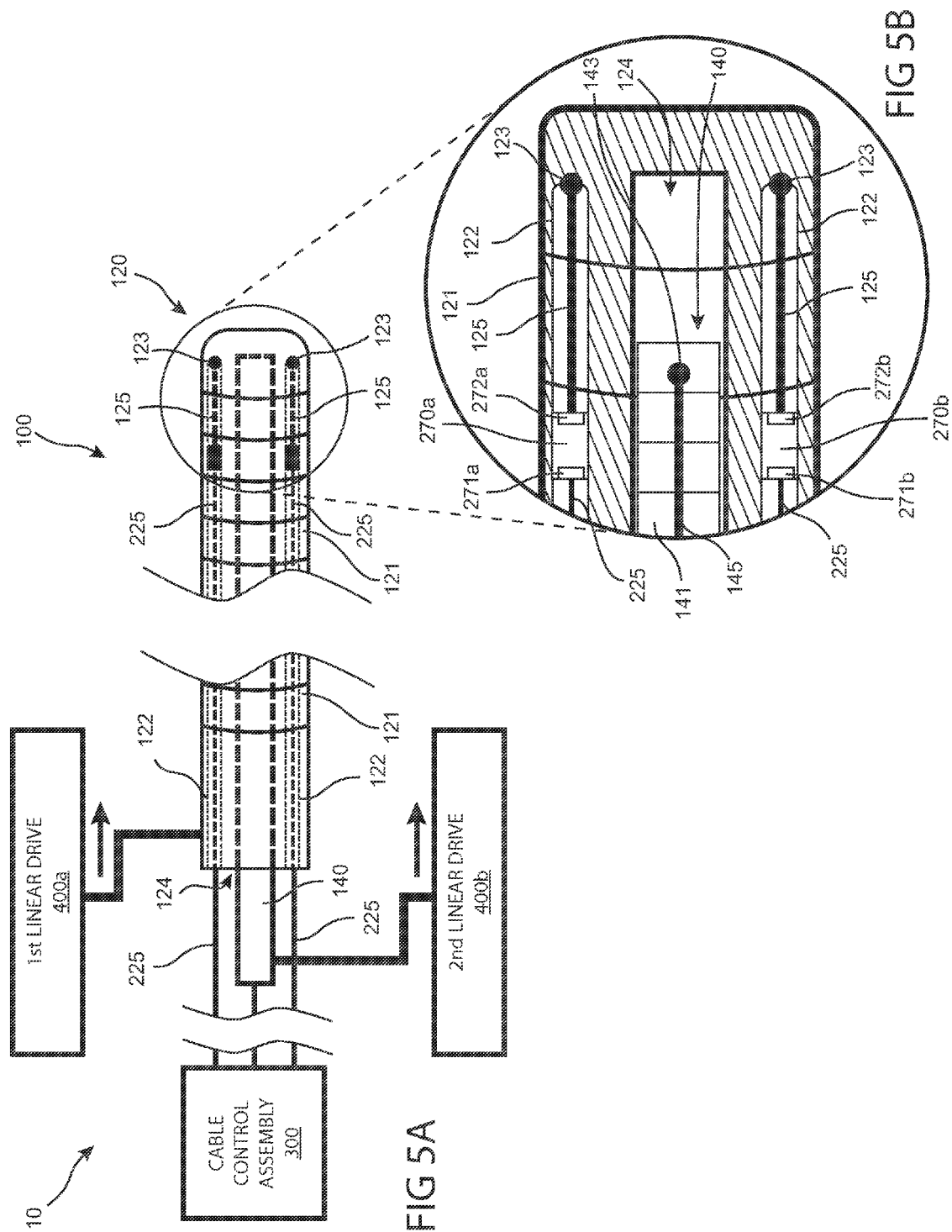

ROBOTIC SYSTEM INCLUDING A CABLE INTERFACE ASSEMBLY

RELATED APPLICATIONS

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. patent application Ser. No. 13/880,525, filed Apr. 19, 2013, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No. PCT/US12/40414, filed Jun. 1, 2012, the content of which is incorporated herein by reference in its entirety.

This application related to U.S. patent application Ser. No. 14/119,316, filed Nov. 21, 2013, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2011/060214, filed Nov. 10, 2011, the content of which is incorporated herein by reference in its entirety.

This application is related to U.S. patent application Ser. No. 13/884,407, filed May 9, 2013, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No. PCT/US12/32279, filed Apr. 5, 2012, the content of which is incorporated herein by reference in its entirety.

This application is related to U.S. patent application Ser. No. 14/008,775, filed Sep. 30, 2013, the content of which is incorporated herein by reference in its entirety.

This application is related to U.S. Provisional Application No. 61/534,032 filed Sep. 13, 2011, the content of which is incorporated herein by reference in its entirety.

This application is related to PCT Application No. PCT/US12/54802, filed Sep. 12, 2012, the content of which is incorporated herein by reference in its entirety.

This application is related to U.S. patent application Ser. No. 14/343,915, filed Mar. 10, 2014, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 13/812,324, filed Jan. 25, 2013, the content of which is incorporated herein by reference in its entirety.

This application is related to U.S. Provisional Application No. 61/578,582, filed Dec. 21, 2011, the content of which is incorporated herein by reference in its entirety.

This application is related to PCT Application No. PCT/US12/170,924, filed Dec. 20, 2012, the content of which is incorporated herein by reference in its entirety.

This application is related to U.S. Provisional Application No. 61/681,340, filed Aug. 9, 2012, the content of which is incorporated herein by reference in its entirety.

This application is related to PCT Application No. PCT/US13/54326, filed Aug. 9, 2013, the content of which is incorporated herein by reference in its entirety.

This application is related to U.S. Provisional Application No. 61/751,498, filed Jan. 11, 2013, the content of which is incorporated herein by reference in its entirety.

This application is related to PCT Application No. PCT/US14/01808, filed Jan. 9, 2014, the content of which is incorporated herein by reference in its entirety.

This application is related to U.S. Provisional Application No. 61/656,600, filed Jun. 7, 2012, the content of which is incorporated herein by reference in its entirety.

This application is related to PCT Application No. PCT/US13/43858, filed Jun. 3, 2013, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety This application claims the benefit of U.S. Provisional Application No. 61/921,858, filed Dec. 30, 2013, the content of which is incorporated herein by reference in its entirety This application claims the benefit of U.S. Provisional Application No. 61/825,297, filed May 20, 2013, the content of which is incorporated herein by reference in its entirety.

This application claims the benefit of U.S. Provisional Application No. 61/818,878, filed May 2, 2013, the content of which is incorporated herein by reference in its entirety.

This application claims the benefit of U.S. Provisional Application No. 61/909,605, filed Nov. 27, 2013, the content of which is incorporated herein by reference in its entirety.

FIELD

Embodiments of the inventive concepts relate generally to the field of robotics and, more particularly, to three-dimensional, flexible, steerable robotic devices, and methods of forming and controlling the same.

BACKGROUND

As less invasive medical techniques and procedures become more widespread, medical professionals, such as surgeons, may employ snake-like robotic systems having highly articulated multi-link probes to access parts of the human anatomy that were otherwise difficult to reach. With the use of such robotic systems, medical professionals may be able to replace open-cavity surgical procedures with less invasive procedures.

Such articulating probes can be subject to significant forces in order to control or lock the linking mechanism, and subject the probe to undesired movements and adversely affect the performance of the articulating probe.

SUMMARY

In an aspect, a system for performing a medical procedure is provided. The system comprises: a first multi-linked mechanism comprising a plurality of first links, a proximal end, a distal end and a lumen therethrough; wherein the first multi-linked mechanism is constructed and arranged to transition from a limp state to a rigid state; a second multi-linked mechanism comprising a plurality of second links, wherein the second multi-linked mechanism is constructed and arranged to be slidingly received by the lumen of the first multi-linked mechanism and to transition from a limp state to a rigid state; a set of proximal cables comprising at least a first proximal cable and a second proximal cable; a set of distal cables comprising at least a first distal cable and a second distal cable; a cable control assembly constructed and arranged to independently apply tension to the first proximal cable and the second proximal cable; a cable interface assembly constructed and arranged to receive a force from at least the first proximal cable and the second proximal cable and to transmit a corresponding force to at least the first distal cable and the second distal cable. The system can be constructed and arranged such that the force applied to the first distal cable and the second distal cable steers the first multi-linked mechanism and/or the second multi-linked mechanism.

The system can comprise a first portion and a second portion and wherein at least the first portion is constructed and arranged to be used in multiple medical procedures. The first portion can comprise at least one of: an input portion of the cable interface assembly; the set of proximal cables; a user interface of the system; the cable control assembly; a pulley of the system; a linear drive of the system; or the second multi-linked mechanism. The system can further comprise a second portion constructed and arranged to be used in fewer medical procedures than the first portion. The second portion can comprise at least one of: an output portion of the cable interface assembly; the set of distal cables; a pulley of the system; or the first multi-linked mechanism.

The cable interface assembly can comprise a first portion and a second portion, wherein the first portion is constructed and arranged to be used in more medical procedures than the first portion. The first portion can comprise an input constructed and arranged to attach to the set of proximal cables and the second portion can comprise an output constructed and arranged to attach to the set of distal cables. The second portion can be constructed and arranged to be used in a single medical procedure.

The cable interface assembly can comprise an input constructed and arranged to attach to the set of proximal cables and an output constructed and arranged to attach to the set of distal cables.

The cable interface assembly can be constructed and arranged to transmit a first force to the first distal cable and a second force to the second distal cable simultaneously.

The cable interface assembly can be constructed and arranged to transmit a first force to the first distal cable and a second force to the second distal cable sequentially.

The cable interface assembly can be constructed and arranged to provide a mechanical advantage between the proximal cables and the distal cables. The mechanical advantage can comprise a proportional mechanical advantage. The mechanical advantage can comprise a disproportional mechanical advantage. The mechanical advantage can comprise an increase in force transmitted between a proximal cable and a distal cable. The mechanical advantage can comprise an increase in translation distance transmitted between a proximal cable and a distal cable.

The cable interface assembly is positioned proximal to the first and second multi-linked mechanisms. The cable interface assembly can be positioned within the first multi-linked mechanism. The cable interface assembly can be positioned within the second multi-linked mechanism.

The cable interface assembly can comprise at least one gimbal. The at least one gimbal can comprise an input surface that attaches to the set of proximal cables and an opposing output surface that attaches to the set of distal cables. The at least one gimbal can comprise at least two gimbals. The at least two gimbals can comprise a first gimbal that rotates about a first axis and a second gimbal that rotates about a second axis oriented relatively 90° to the first axis.

The cable interface assembly can comprise at least one multi-diameter pulley. The at least one multi-diameter pulley can comprise a first pulley that attaches to the first proximal cable and the first distal cable, and a second pulley that attaches to the second proximal cable and the second distal cable. The cable interface assembly can further comprise at least one brake assembly constructed and arranged to apply a braking force to the at least one multi-diameter pulley.

The cable interface assembly can be constructed and arranged to amplify translation between the first proximal cable and the first distal cable. The amplification can comprise an amplification ratio selected from the group consisting of: 1:100:1:50; 1:25:1:10; 1:5:1:2:1:1; 2:1:5:1:10:1; 25:1; 50:1; 100:1; and combinations thereof. The cable interface assembly comprises a first multi-diameter pulley and a second multi-diameter pulley. The cable interface assembly can be constructed and arranged to provide a different amplification between the second proximal cable and the second distal cable.

The cable interface assembly can be constructed and arranged to amplify force applied between the first proximal cable and the first distal cable. The amplification can comprise an amplification ratio selected from the group consisting of: 1:100:1:50; 1:25:1:10; 1:5:1:2:1:1; 2:1:5:1:10:1; 25:1; 50:1; 100:1; and combinations thereof. The cable interface assembly can comprise a first multi-diameter pulley and a second multi-diameter pulley. The cable interface assembly can be constructed and arranged to provide a different amplification between the second proximal cable and the second distal cable.

The system can further comprise a second cable interface assembly constructed and arranged to receive a force from at least one cable and transmit a force to at least one cable. The second cable interface assembly can be dissimilar to the first cable interface assembly. The system can further comprise a control conduit between the first and second cable interface assemblies. The second cable interface assembly can be positioned in series with the first cable interface assembly. The system can further comprise a middle set of cables positioned between and operably attached to the first cable interface assembly and the second cable interface assembly. The second cable interface assembly can be attached to a second set of proximal cables and a second set of distal cables.

The distal cables can be constructed and arranged to steer the first multi-linked mechanism. The distal cables can be constructed and arranged to steer the second multi-linked mechanism.

One or more proximal cables and one or more distal cables can comprise different construction. The different construction can comprise a different construction property selected from the group consisting of: elasticity; flexibility; pushability; column strength; torqueability; diameter; materials of construction; braiding parameter such as pitch or pick count; and combinations thereof.

The set of proximal cables can be operably attached to the cable interface assembly in a first pattern and the set of distal cables are operably attached to the cable interface assembly in a second pattern. The first pattern and the second pattern can comprise similar geometric patterns. The first pattern and the second pattern can comprise dissimilar geometric patterns.

The set of proximal cables can comprise a first quantity and the set of distal cables can comprise a second quantity similar to the first quantity. The set of proximal cables can comprise a first quantity and the set of distal cables can comprise a second quantity different than the first quantity. The quantity of proximal cables can be more than the quantity of distal cables. The quantity of proximal cables can be less than the quantity of distal cables.

The system can further comprise one or more pulleys. The one or more pulleys can operably engage a portion of at least one proximal cable. The one or more pulleys can operably engage a portion of at least one distal cable.

The system can further comprise at least one linear drive. The at least one linear drive can be attached to the first multi-linked mechanism and the cable interface assembly. The system can further comprise a second cable interface assembly and a second linear drive attached to the second multi-linked mechanism and the second cable interface assembly. The at least one linear drive can be attached to the second multi-linked mechanism and the cable interface assembly.

The system can further comprise a linear compensator constructed and arranged to allow motion between the cable interface assembly and at least one of the first multi-linked mechanism and the second multi-linked mechanism. The linear compensator can comprise a spring. The linear compensator can comprise an element selected from the group consisting of: a spring; a linear actuator; a magnet; a piston; a compressible element; and combinations thereof.

The system can further comprise a sensor constructed and arranged to measure a parameter of the cable interface assembly. The parameter can comprise a parameter selected from the group consisting of: displacement; force; pressure; velocity; proximity; acceleration; strain; and combinations thereof. The sensor can comprise a sensor selected from the group consisting of: a pressure sensor; a strain gauge; a magnetic sensor such as a Hall effect sensor; a piezoelectric sensor; a capacitive sensor; and combinations thereof. The sensor can be constructed and arranged to quantify a parameter of the cable interface assembly selected from the group consisting of: an amplification of proximal to distal cable translation; an amplification of proximal to distal cable tension; an angular rotation of a component of the cable interface assembly such as a rotating gimbal or a rotating pulley; a linear displacement of a component of the cable interface assembly; a linear displacement of a proximal cable; a linear displacement of a distal cable; tension in a proximal cable; tension in a distal cable; and combinations thereof.

The first multi-linked mechanism can further comprise at least one sideport. The first multi-linked mechanism can further comprise at least two channels each constructed and arranged to slidingly receive one of the first or second distal cables.

The set of distal cables can further comprise a third distal cable, wherein the first multi-linked mechanism comprises at least three channels each constructed and arranged to slidingly receive one of the first, second, or third distal cables.

The system can further comprise at least one working channel between the first multi-linked mechanism and the second multi-linked mechanism.

The system can further comprise a user interface.

The system can further comprise a tool with a flexible distal portion. The system can further comprise a lumen for slidingly receiving at least a distal portion of the tool. The lumen can be positioned in at least one of: a sideport of the first multi-linked mechanism; a Lumen of the first multi-linked mechanism; a lumen of the second multi-linked mechanism; or a working channel positioned between the first multi-linked mechanism and the second multi-linked mechanism. The tool can comprise one or more tools selected from the group consisting of: cameras, light or other radiation sources, cutters, graspers, scissors, energy appliers, suturing assemblies, biopsy removal elements, ventilators, lasers, cautery, clip appliers, scissors, needles, needle drivers, scalpels, RF energy delivery devices, cryogenic energy delivery devices, drug delivery devices, EKG electrodes, pressure sensors, a blood sensors, magnets, heating elements, and combinations thereof.

According to another aspect, a method of performing a medical procedure comprises selecting a system in accordance with an aspect of the inventive concepts; and performing a medical procedure using the system.

According to another aspect, a system as described in reference to the drawings is provided.

According to another aspect, a method as described in reference to the drawings is provided.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The technology described herein, along with the attributes and attendant advantages thereof, will best be appreciated and understood in view of the following detailed description taken in conjunction with the accompanying drawings in which representative embodiments are described by way of example.

FIG. 5A is a schematic view of a system for performing a medical procedure, consistent with the present inventive concepts.

FIG. 5B is a magnified view of the distal portion of a probe of the system of FIG. 5A, consistent with the present inventive concepts.

DETAILED DESCRIPTION OF THE DRAWINGS

Figure 1:
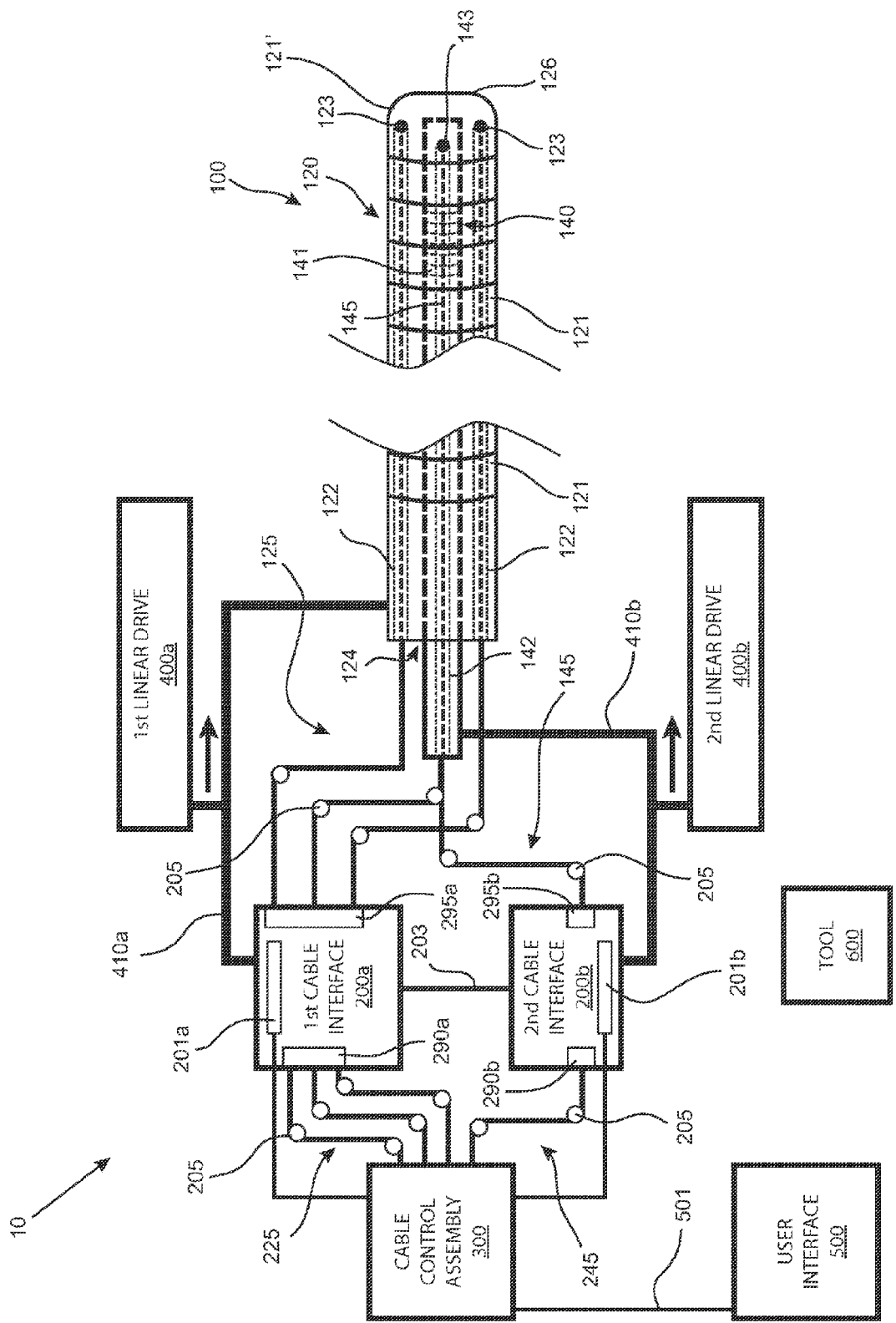
FIG. 1 is a schematic view of a system for performing a medical procedure, consistent with the present inventive concepts.

Reference will now be made in detail to the present embodiments of the technology, examples of which are illustrated in the accompanying drawings. The same reference numbers are used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination.

For example, it will be appreciated that all features set out in any of the claims (whether independent or dependent) can be combined in any given way.

Referring now to FIG. 1, a schematic view of a system for performing a medical procedure is illustrated, consistent with the present inventive concepts. System 10 can be constructed and arranged as a robotic introducer system for performing a medical procedure, such as a transoral robotic surgery procedure. System 10 can include one or more features of a surgical positioning and support system, for example, as described in U.S. patent application Ser. No. 13/812,234, filed Jan. 25, 2013, U.S. patent application Ser. No. 13/812,324, filed Jul. 21, 2011, U.S. patent application Ser. No. 14/008,775, filed Apr. 5, 2012, and International PCT Application Number PCT/US2013/054326, filed Aug. 9, 2013, the contents of each being incorporated herein by reference in their entirety.

System 10 can be constructed and arranged to position one or more tools (not shown) for performing a medical procedure on a patient, for example, a transoral robotic surgery procedure or the like, or other surgical procedure that includes inserting one or more tools into a cavity of the patient, or a region of the patient formed by an incision or related opening. A surgical procedure can include one or more transoral procedures, including but not limited to resections at or near the base of a tongue, tonsils, a base of a skull, hypopharynx, larynx, trachea, esophagus and within the stomach and small intestine. Other medical procedures can include but not be limited to single or multiple transaxilla procedures, such as a laryngectomy; single or multiple thoracoscopic procedures, such as a mediastinal nodal dissection; single or multiple pericardial procedures, for example, related to measuring and treating arrhythmias; single or multiple laparoscopic procedures, such as revision of bariatric lap-band procedures; single or multiple transgastric or transenteric procedures, such as a cholecystectomy or splenectomy; and/or single or multiple transanal or transvaginal procedures, such as a hysterectomy, oophorectomy, cystectomy and colectomy.

System 10 includes a probe 100 comprising a first multi-linked mechanism, outer probe 120, and a second multi-linked mechanism, inner probe 140. Outer probe 120 includes a lumen 124 configured to slidingly receive inner probe 140, where lumen 124 terminates at a location proximal to distal end 126 of outer probe 120. System 10 includes multiple flexible filaments ("cables") configured to apply forces to control one or more parameters of outer probe 120 and inner probe 140, as described in detail herebelow. System 10 can include one or more pulleys, such as pulleys 205 shown in FIG. 1, which operably engage one or more cables of system 10, such as to allow a cable to assume a non-linear path from its proximal end to its distal end and efficiently transmit applied forces along its length. System 10 includes a set of one or more cables 125 (e.g. the three cables 125 shown in FIG. 1). Cables 125 can be constructed and arranged to control outer probe 120, such as to steer, change the rigidity of, maintain the rigidity of and/or otherwise control outer probe 120. System 10 can also include an additional set of one or more cables 145 (e.g. the single cable 145 shown in FIG. 1). Cables 145 can be constructed and arranged to control inner probe 140, such as to steer, change the rigidity of, maintain the rigidity of and/or otherwise control inner probe 140. In some embodiments, probe 100, outer probe 120, inner probe 140 and cables 125 and 145 are constructed and arranged as has been described in applicant's co-pending application International PCT Application Serial Number PCT/US2012/70924, filed Dec. 20, 2012, the content of which is incorporated herein by reference in its entirety, such as to be advanced, retracted, steered, transitioned between a rigid mode and a flexible mode, and/or otherwise operated to support system 10. Changing the rigidity of outer probe 120 and/or inner probe 140 includes transitioning between a limp mode and a rigid mode.

System 10 includes at least one cable interface 200, such as cable interface 200a or cable interface 200b as shown. Each cable interface 200 comprises an input 290 (e.g. inputs 290a and 290b shown) configured to operably attach to a set of controlling cables, such as proximal cables 225 or 245. Each cable interface 200 further comprises an output 295 (e.g. outputs 295a and 295b shown) configured to operably attach to a set of cables to be controlled, such as distal cables 125 or 145. Each cable interface 200 can be constructed and arranged to provide a mechanical advantage between one or more cables attached in input 290 and one or more cables attached to output 295. Input 290 and output 295 are operably connected to each other with one or more mechanisms of cable interface 200 that are configured such that any motion and/or forces applied to interface 200 by one or more attached proximal cables, causes a resultant motion and/or forces to be applied by interface 200 to one or more attached distal cables. Various mechanisms, such as those described herein, can be used to proportionally or disproportionally translate an input signal (e.g. force or motion) applied to input 290 to an output signal (e.g. force or motion) applied by output 295.

Cables 125, which control outer probe 120, can be attached to and controlled by cable interface 200a. Cable interface 200a is attached to and is controlled by a set of cables 225 which are in turn controlled by cable control assembly 300. In these embodiments, cables 125 are referred to as a set of one or more distal cables (i.e. distal to cable interface 200a) and cables 225 are referred to as a set of one or more proximal cables (i.e. proximal to cable interface 200a). Cable interface 200a is constructed and arranged to control distal cables 125 based on the forces applied to cable interface 200a by proximal cables 225. Alternatively, cables 125 can attach directly to and be controlled by cable control assembly 300 (i.e. when system 10 does not include cable interface 200a nor proximal cables 225).

Cables 145, which control inner probe 140, can be attached to and controlled by cable interface 200b. Cable interface 200b is attached to and is controlled by a set of cables 245 which are in turn controlled by cable control assembly 300. In these embodiments, cables 145 are referred to as a set of one or more distal cables (i.e. distal to cable interface 200b) and cables 245 are referred to as a set of one or more proximal cables (i.e. proximal to cable interface 200b). Cable interface 200b can be constructed and arranged to control one or more distal cables, such as distal cable 145, based on the forces applied to cable interface 200b by one or more proximal cables 245. Alternatively, cables 145 can attach directly to and be controlled by cable control assembly 300 (i.e. when system 10 does not include cable interface 200b nor proximal cables 245).

In some embodiments, system 10 includes cable interface 200a but does not include cable interface 200b (i.e. cables 145 attach to and are controlled directly by cable control assembly 300). In other embodiments, system 10 includes cable interface 200b but does not include cable interface 200a (i.e. cables 125 attach to and are controlled directly by cable control assembly 300). In some embodiments, multiple cable interfaces 200 are connected in series, such that a middle set of cables (not shown) are controlled by a proximal set of cables (e.g. cables 225 or 245), each attached to an output and input, respectively of a first cable interface 200. A distal set of cables (e.g. cables 125 or 145) are controlled by the middle set of cables, each attached to an output and input, respectively, of a second cable interface 200. Alternatively or additionally, in some embodiments, cable interface 200a is operably connected or otherwise influenced by cable interface 200b, such as via a control conduit 203 constructed and arranged to transfer a force, motion or control signal between cable interface 200a and 200b to adjust the operation of either or both.

Cable interface 200a and 200b can be of similar or dissimilar construction. Cable interface 200a and/or 200b, collectively cable interface 200, can be configured to apply a mechanical advantage between the proximal and distal cables, such as to improve or enhance (hereinafter "improve") the control of outer probe 120 and/or inner probe 140. For example, a mechanical advantage applied by cable interface 200a between proximal cables 225 and distal cables 125 can be configured to provide improved steering of outer probe 120, such as smoother or more precise steering. Alternatively or additionally, a mechanical advantage can be applied by cable interface 200a to achieve greater steering or locking forces for outer probe 120. Similarly improvements can be achieved with cable interface 200b in the control of inner probe 140.

In some embodiments, proximal cables 225 or 245, cable interface 200a or cable interface 200b, and distal cables 125 or 145, respectively, are attached (e.g. in a particular pattern of attachment) and are otherwise constructed and arranged such that a translation or force applied by each proximal cable to cable interface 200 results in a proportional (e.g. a proportionally amplified or attenuated) response in the translation or force applied by cable interface 200 to each corresponding distal cable. In these proportional transfer configurations, the proximal cables can be attached to a portion of cable interface 200 in a first geometric pattern (e.g. in a triangular pattern attached to one side of a gimbal), and the distal cables can be attached to a portion of the cable interface in a second geometric pattern similar to the first geometric pattern (e.g. a triangular pattern attached to the opposite side of the gimbal), such as is described in the gimbal design described in reference to FIGS. 2-3 herebelow. Alternatively, the first and second geometric patterns can be different. In some embodiments, each proximal cable is operably attached to a first diameter portion of a multiple diameter pulley, and each distal cable can be operably attached to a corresponding second diameter portion of the corresponding pulley, such as is described in reference to FIG. 4 herein. In other embodiments, cable interface 200 can be constructed and arranged such that translation or force applied by proximal cables can result in a disproportional translation or force applied to distal cables. In these embodiments, the resultant force or translation, although not proportional, is known and/or otherwise can be determined by system 10 and can be used by one or more components of system 10 to control outer probe 120 or inner probe 140. In these embodiments, different patterns of cable attachment to cable interface can be used, different numbers of proximal versus distal wires can be included, and the like, with a known transfer response of cable interface 200.

In some embodiments, a cable interface 200 is configured such that a relative proximal cable translation (e.g. linear advancement or retraction of a cable 225 or 245) results in less translation in distal cables (e.g. less advancement or retraction of a corresponding cable 125 or 145 respectively). In these mechanisms configured for proportionally attenuating cable translation, the force applied to the distal cables by cable interface 200 is proportionally increased (e.g. a 1:2 ratio of proximal to distal cable translation corresponds to a 2:1 ratio of applied proximal cable tension to resultant distal cable tension). In other embodiments, a cable interface 200 is configured such that a relative proximal cable translation results in more translation in the corresponding distal cable. In these mechanisms configured for proportionally amplifying cable translation, the force applied to the distal cable by cable interface 200 is proportionally decreased (e.g. a 2:1 ratio of proximal to distal cable translation corresponds to a 1:2 ratio of applied proximal cable tension to resultant distal cable tension). Cable interface 200 can be constructed and arranged to have a broad range of amplification or attenuation (hereinafter "amplification") of cable translation, such as an amplification of: 1:100:1:50; 1:25:1:10; 1:5:1:2:1:1; 2:1:5:1:10:1; 25:1; 50:1; or 100:1. Cable interface 200 can be constructed and arranged to have a broad range of amplification of applied proximal cable tension to resultant distal cable tension, such as an amplification of: 1:100:1:50; 1:25:1:10; 1:5:1:2:1:1; 2:1:5:1:10:1; 25:1; 50:1; or 100:1. Cable interface 200 can comprise various constructions that amplify or attenuate cable translation and/or applied tension, proportionally or otherwise.

In some embodiments, cable interface 200 applies a first amplification level to a first corresponding pair of proximal and distal cables, and a second, different amplification level to a second corresponding pair of proximal and distal cables, wherein the first pair and second pair are each attached to the same cable interface 200. The first and second amplification levels can be each be proportional or disproportional amplification levels.

System 10 includes a first linear drive 400*a* constructed and arranged to allow outer probe 120 to be advanced and retracted. Linear drive 400*a* is attached to a proximal portion of outer probe 120 via connector 410*a* as shown. Linear drive 400*a* can be attached to and controlled by cable control assembly 300, attachment not shown but typically one or more wires or other information and/or power conduits. In embodiments where system 10 includes cable interface 200*a*, connector 410*a* is further attached to cable interface 200*a* such that interface 200*a* and outer probe 120 move in unison. System 10 further includes a second linear drive 400*b* constructed and arranged to allow inner probe 140 to be advanced and retracted. Linear drive 400*b* is attached to a proximal portion of inner probe 140 with connector 410*b* as shown. Linear drive 400*b* can be attached to and controlled by cable control assembly 300, attachment not shown but typically one or more wires or other information and/or power conduits.

In some embodiments, cable interface 200 comprises a sensor, such as sensor 201*a* and/or 201*b* of cable interfaces 200*a* and/or 200*b*, respectively. Sensor 201*a* and/or 201*b*, collectively sensor 201, can be a sensor constructed and arranged to measure displacement, force, pressure, velocity, proximity, acceleration, strain and/or another parameter. In some embodiments, sensor 201*a* and/or 201*b* comprises a sensor selected from the group consisting of: a pressure sensor; a strain gauge; a magnetic sensor such as a Hall effect sensor; a piezoelectric sensor; a capacitive sensor; and combinations of these. Sensor 201 can be configured to quantify a parameter selected from the group consisting of: the amplification of proximal or distal cable translation; the amplification of applied proximal cable tension to resultant distal cable tension; angular rotation of a component of cable interface 200 (e.g. a rotating gimbal or pulley); linear displacement of a component of cable interface 200 or a cable of system 10; tension in a cable of system 10; and combinations of these.

Cable control assembly 300 can comprise one or more drive mechanisms such as motors, which independently drive (e.g. advance and retract) multiple supplies of cable, such as cables wrapped around bobbins that are motor-driven. In some embodiments, cable control assembly 300 is constructed and arranged as described in applicant's co-pending application International PCT Application Serial Number PCT/US2012/70924, filed Dec. 20, 2012, the content of which is incorporated herein by reference in its entirety.

Outer probe 120 includes multiple links 121 terminating in distal link 121', collectively links 121. Each link 121 includes one or more channels 122 that slidingly receive a cable 125. Each cable 125 extends through a channel of each link 121 and terminates at its distal end at anchor point 123. In some embodiments, each link 121 of outer probe 120 comprises three channels separated by approximately 120° along an inner circumference of each link 121. In embodiments where cables 125 comprise multiple cables, cables 125 can be used to steer as well as lock outer probe 120. Alternatively, cables 125 can comprise a single cable 125, such as a single cable 125 that is used to transition outer probe 120 between a limp and rigid mode and/or to partially steer outer probe 120.

Inner probe 140 includes multiple links 141 which can include one or more channels, such as a single channel 142 which extends to a distal link of inner probe 140. In some embodiments, cable 145 comprises a single cable 145 which extends through channel 142 and terminates at its distal end at anchor point 143. In these single cable 145 embodiments, cable 145 is used to transition inner probe 140 between a limp and rigid mode. Alternatively, cables 145 can comprise multiple cables, such as when channel 142 comprises three channels separated by approximately 120°, and cables 145 are positioned within the three channels 142 to both transition inner probe 140 between a limp and rigid mode, as well as steer inner probe 140. In some embodiments, cable interface 200*a* and/or 200*b* are positioned between the proximal and distal ends of outer probe 120 and/or inner probe 140, such as is described in reference to FIG. 5A-B herebelow.

System 10 comprises a user interface 500 which can be attached at least to cable control assembly 300 via conduit 501. Conduit 501 can include one or more wires or other information and/or power conduits. User interface 500 can comprise one or more user interface components selected from the group consisting of: a joystick; a mouse; a keyboard; a touch pad; a video monitor; an indicator light; an alarm transducer; a touch screen; a printer; and combinations thereof. User interface 500 and/or cable control assembly 300 include one or more electronic modules including algorithms, transfer functions and/or other software used to convert user input commands (e.g. from a joystick) to control signals. Control signals can be used to perform a function selected from the group consisting of: advancing and retracting cables, such as cables 225, 245, 125 and/or 145; advancing and/or retracting outer probe 120 and/or inner probe 140 via first linear driver 400*a* and/or second linear drive 400*b*; activating, manipulating and/or otherwise controlling one or more tools 600; and combinations thereof. In some embodiments, user interface 500 is constructed and arranged as described in applicant's co-pending U.S. patent application Ser. No. 14/119,316, filed Jun. 1, 2012, the contents of which is incorporated herein by reference in its entirety.

System 10 can include one or more tools 600, such as one or more surgical tools with a flexible distal portion. Tool 600 can include a flexible shaft configured to pass through a location selected from the group consisting of: one or more channels of inner probe 140; one or more channels of outer probe 120; one or more channels positioned between inner probe 140 and outer probe 120 (e.g. a series of corresponding grooves aligned between the multiple links 121. Tool 600 can comprise a tool selected from the group consisting of: cameras, light or other radiation sources, cutters, graspers, scissors, energy appliers, suturing assemblies, biopsy removal elements, ventilators, lasers, cautery, clip appliers, scissors, needles, needle drivers, scalpels, RF energy delivery devices, cryogenic energy delivery devices, drug delivery devices, EKG electrodes, pressure sensors, a blood sensors, magnets, heating elements, or combinations of these. In some embodiments, outer probe 120 includes one or more sideports, not shown but such as one or more sideports comprising a radial projection from a link 121, wherein the radial projection comprises a lumen configured to slidingly receive one or more tools of system 10, such as tool 600. In some embodiments, outer probe 120 includes one or more sideports such as those described in applicant's co-pending U.S. patent application Ser. No. 13/812,324, filed Jul. 21, 2011, the content of which is incorporated herein by reference in its entirety.

The proximal and distal cables of system 10, such as proximal cables 225 and 245, and corresponding distal cables 125 and 145, respectively, can have similar or dissimilar construction. In some embodiments, the proximal and distal cables have a dissimilar property selected from the group consisting of: elasticity; flexibility; pushability; column strength; torqueability; diameter; materials of construction; braiding parameter such as pitch or pick count; and combinations of these.

In some embodiments, a first quantity of proximal cables are received from cable control assembly 300 by an input 290 of a cable interface 200, and a second, similar quantity of distal cables are received by outer probe 120 or inner probe 140 by an output 295 of the cable interface 200. In some embodiments, a first quantity of controlling proximal cables (e.g. proximal cables 225 or 245) attach to input 290 of cable interface 200, and a second, different quantity of controlled distal cables (e.g. distal cables 125 or 145) are attached to output 295 of cable interface 200. In these embodiments, the quantity of input cables can be greater than or less than the quantity of output cables. In some embodiments, the quantity of cables attached to input 290 is the same as the quantity of cables attached to output 295, however the pattern of attachment can be different.

In some embodiments, one or more portions of system 10 are re-used, such are one or more portions that are maintained outside of the sterile barrier of a medical procedure and/or are re-sterilized between a first medical procedure and a second medical procedure. In some embodiments, a cable interface 200 comprises a first portion and a second portion, where the first portion includes input 290 and the second portion includes output 295. In these embodiments, the first portion can be re-used as described above, and/or it can otherwise be used more times than the second portion is used, such as when the each first portion is used with multiple second portions such as multiple portions including output 295 that are disposed of after each medical procedure. In some embodiments, the first portion and second portion of cable interface 200 is configured as described in reference to FIGS. 6A-6B described herebelow. In these re-use embodiments, in addition to input 290 and output 295, one or more other components or portions of system 10 can be constructed and arranged for re-use or single use. In some embodiments, at least one of the following components are used in multiple medical procedures: input 290a; input 290b; proximal cables 225; proximal cables 245; user interface 500; cable control assembly 300; one or more pulleys 205; first linear drive 400a; second linear drive 400b; or inner probe 140. In some embodiments, at least one of the following components are used fewer times, or in a single medical procedure: output 295a; output 295b; distal cables 125; distal cables 145; one or more pulleys 205; or outer probe 120.

Figure 2:
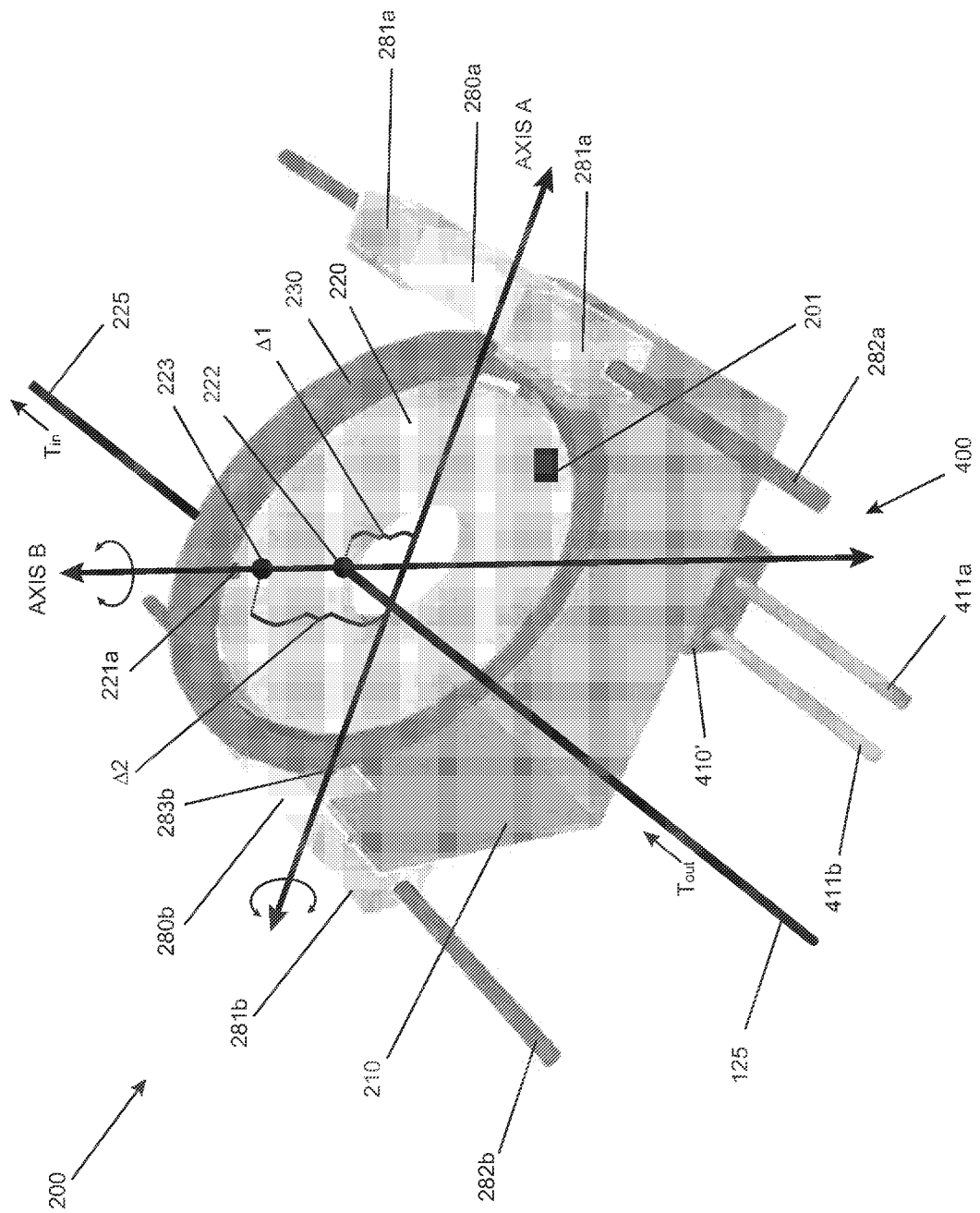
FIG. 2 is a perspective view of a cable interface comprising a two-gimbal design, consistent with the present inventive concepts.
Figure 3:
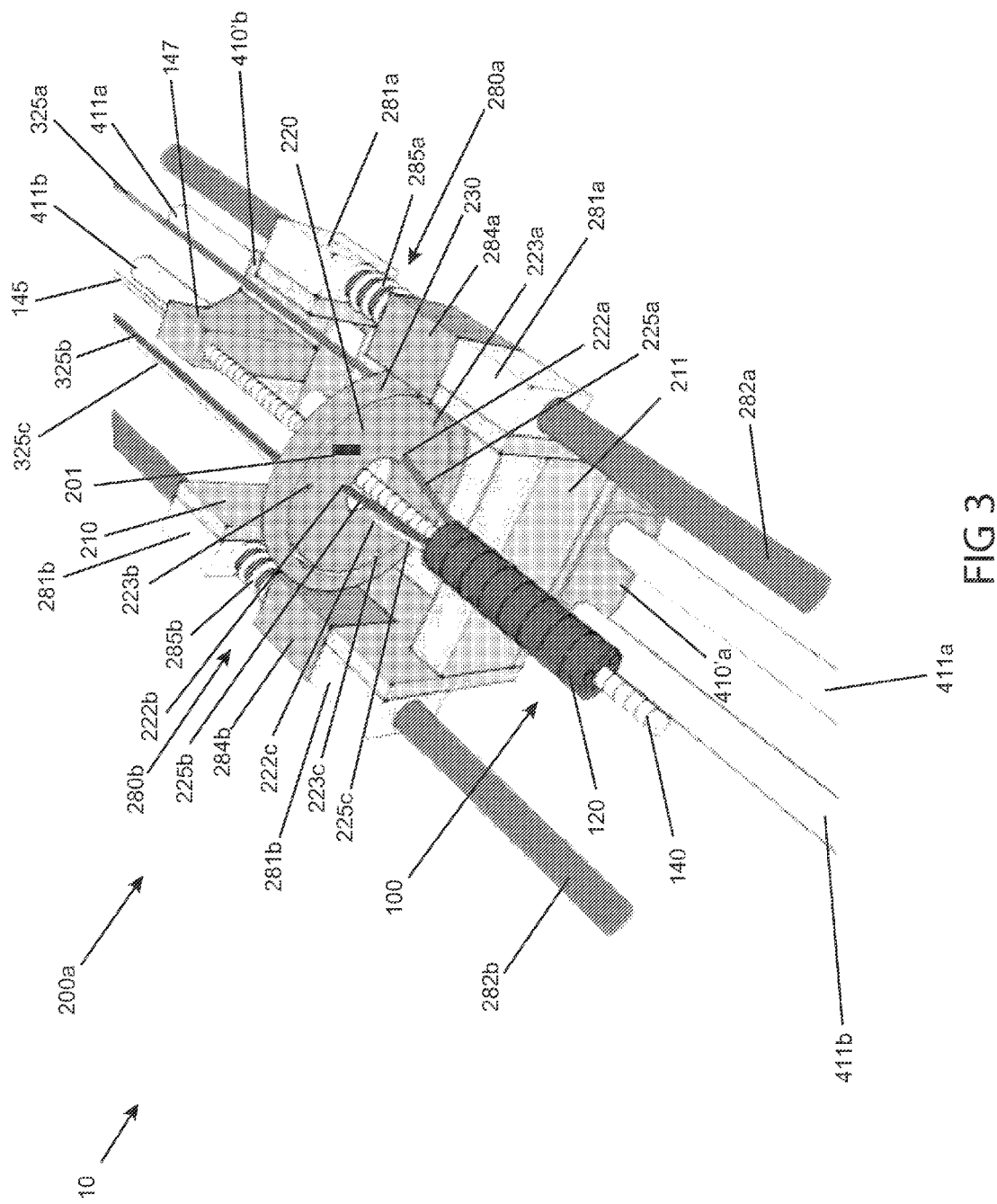
FIG. 3 is a perspective view a portion of a system for performing a medical procedure, consistent with the present inventive concepts.

Referring now to FIG. 2, a perspective view of a cable interface is illustrated, consistent with the present inventive concepts. In some embodiments, cable interface 200 comprises a two-gimbal design having inner ring 220 and outer ring 230. Inner ring 220 is fixed to outer ring 230 at pivot points 221a and 221b (221b not shown but positioned on Axis B on the opposite side of inner ring 220) and can rotate about Axis B. Outer ring 230 is fixed to linear compensators 280a and 280b at pivot points 283a and 283b (283a not shown but positioned on Axis A on the opposite side of outer ring 230), respectively, and can rotate about Axis A. Rotation of outer ring 230 about Axis A allows a second degree of freedom of inner ring 220 about Axis A. Inner ring 220 comprises at least two connection points 222 and 223. Connection point 222 is configured to receive distal cable 125, and connection point 223 is configured to receive proximal cable 225, both distal and proximal cables discussed in FIG. 1 hereabove. Inner ring 220 can comprise more than two connection points, for example where the system comprises more than one proximal cable and/or more than one distal cable, as shown in FIG. 3.

The distance between the intersection point of Axis A and Axis B (hereinafter "origin") and connection points 222 and 223 can be represented by Δ1 and Δ2, respectively. Cable 225 applies a tension $T_{in}$ to inner ring 220. In embodiments in which the pattern of attachment of one or more cables 225 is of similar geometry and alignment (e.g. connection points 222 and 223 are radially aligned) to the pattern of attachment of one or more cables 125, the resultant tension $T_{out}$ applied to cable 125 is equal to $T_{in}$ multiplied by the ratio of Δ1/Δ2. For example, if Δ2 is two times Δ1, then a tension $T_{in}$ applied to cable 225 will result in a tension $T_{out}$ being applied to cable 125 equal to two times $T_{in}$.

Linear drive assembly 400 comprises connector 410' configured to translate along guide rods 411a and 411b and translate carriage 210. Guide rods 411a and/or 411b can be configured as a linear drive or a lead screw as described herebelow.

Interface 200 can translate along guide rods 282a and 282b via adaptors 281a and 281b, respectively. Guide rods 282a and 282b can be configured to perform one or more functions, for example, maintain alignment of cable interface 200; drive one or more components of cable interface 200, for example carriage 210; or stabilize one or more components of cable interface 200. Adaptors 281a and 281b can comprise a friction reducing component, not shown but for example a bushing or the like. Linear compensators 280a and 280b can translate with respect to adaptors 281a and 281b, respectively, and can be configured to translate outer ring 230, thus also translating inner ring 220. For example, linear compensators 280a and 280b can translate with or independent of adaptors 281a and 281b, respectively. Linear compensator 280*a* and 280*b* can comprise one or more components such as a spring; a linear actuator; a magnet; a piston; a compressible element; and combinations of these.

In some embodiments, cable interface 200 comprises a sensor 201. Sensor 201 can be constructed and arranged to measure one or more parameters or states of cable interface 200. In some embodiments, sensor 201 is similar to sensor 201 described in FIG. 1 hereabove.

Referring now to FIG. 3, a perspective view a portion of a system for performing a medical procedure is illustrated, consistent with the present inventive concepts. System 10 comprises probe 100 having inner probe 140 and outer probe 120; cable interface 200*a*; and a cable control assembly, not shown but the same as or similar to cable control assembly 300 of FIG. 1. Components of probe 100 and interface 200*a* can be configured the same as or similar to those described in FIG. 1 and FIG. 2 hereabove. Probe 140 comprises cable 145, configured to be operably attached to a cable control assembly such as cable control assembly 300 of FIG. 1, such as to control the rigidity of inner probe 140, as described hereabove.

In the illustrated embodiment, inner ring 220 comprises six connection points, connection points 222*a-c* configured to receive distal cables 225*a-c* and connection points 223*a-c* configured to receive proximal cables 325*a-c*, both distal and proximal cables discussed in FIG. 1 and FIG. 2 hereabove.

Adaptor 211 fixedly attaches a proximal portion of outer probe 120 to carriage 210 such as via a weld, glue, or other suitable attachment mechanism. Carriage 210 is fixedly attached to connector 410'*a*. Similarly, support 147 fixedly attaches a proximal portion of inner probe 140 to connector 410'*b*. Connector 410'*b* and connector 410'*a* can translate independently of one another to independently translate support 147 and carriage 210, respectively. In the embodiment shown, components fixedly attached to connector 410'*a* or 410'*b* translate in unison with connector 410'*a* and 410'*b*. In some embodiments, guide rods 411*a* and 411*b* are configured as lead screws, such that rotation of lead screw 411*a* causes translation of connector 410'*a*, and rotation of lead screw 411*b* causes translation of connector 410'*b*.

Linear compensator 280*a* and 280*b* can each comprise pivot assembly 284*a* and 284*b* (generally 284) and a compressible element, spring 285*a* and 285*b* (generally 285), respectively. Pivot assembly 284 can translate along guide rods 282 with or independently of adaptors 281 and can be configured to translate outer ring 230, thus also translating inner ring 220, with respect to carriage 210. Pivot assembly 284 can be translated in a proximal direction independently of carriage 210 such that spring 285 is compressed causing distal cables 223*a-c* to tension similarly.

In some embodiments, cable interface 200 comprises a sensor 201. Sensor 201 can be constructed and arranged to measure one or more parameters or states of cable interface 200. In some embodiments, sensor 201 is similar to sensor 201 described in FIG. 1 hereabove.

Figure 4:
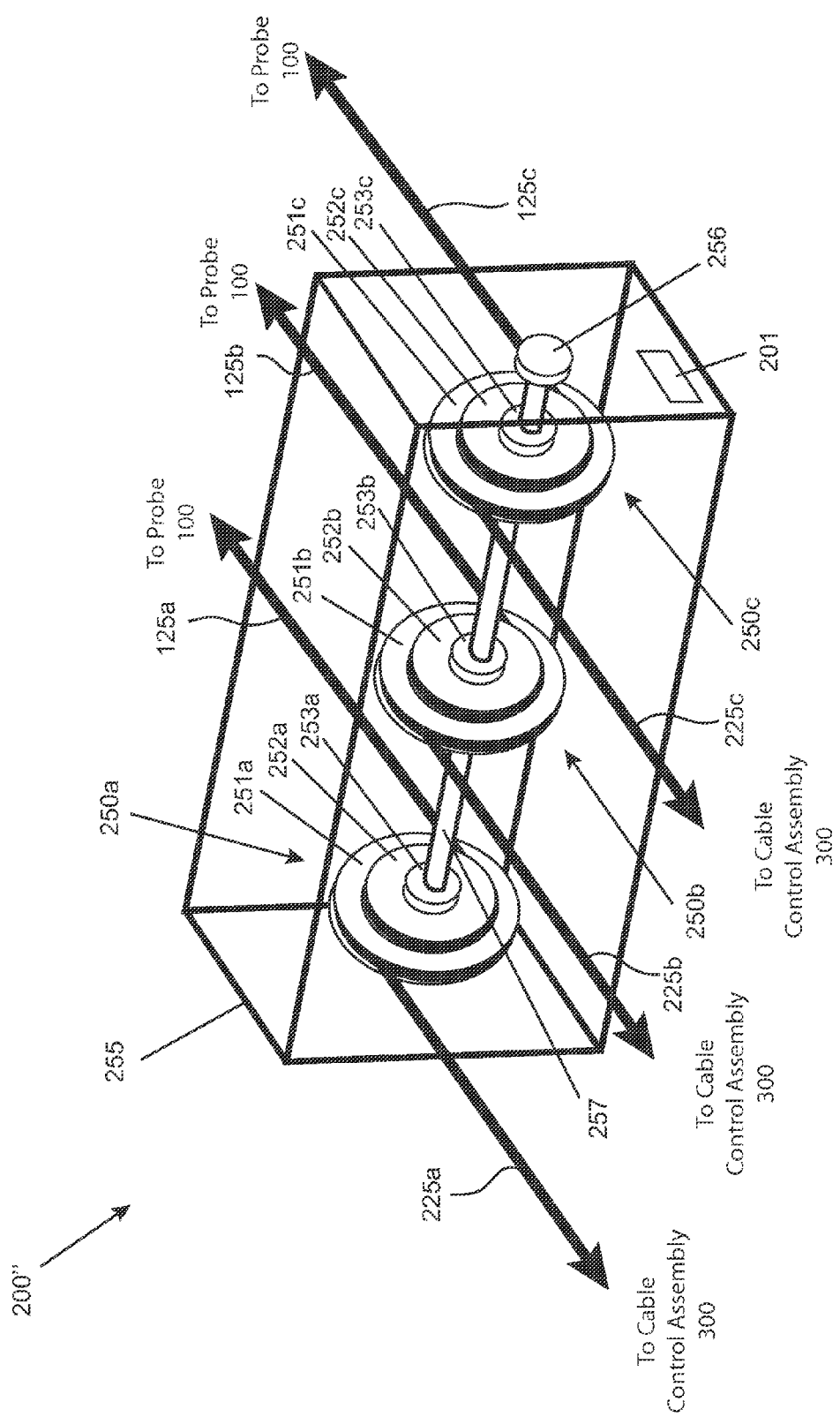
FIG. 4 is a perspective view of a cable interface comprising a pulley design, consistent with the present inventive concepts.

Referring now to FIG. 4, a perspective view of a cable interface is illustrated, consistent with the present inventive concepts. Cable interface 200" comprises pulley assemblies 250*a*, 250*b*, and 250*c*. Each pulley assembly 250*a-c* comprises a first diameter portion 251*a-c*, a second diameter portion 252*a-c*, and a brake assembly 253*a-c*, respectively.

First diameter portions 251*a-c* are operably connected to cables 225*a-c*, respectively, and second diameter portions 252*a-c* are operably connected to cables 125*a-c*, respectively. Cable interface 200" can be constructed and arranged such that translation or force applied by proximal cables 225*a-c* can result in a proportional or a disproportional translation or force applied to distal cables 125*a-c* based on the difference in diameter or shape between first diameter portions 251*a-c* and second diameter portions 252*a-c*. For example, a non-circular diameter portion mated with a circular diameter portion will result in a disproportionally amplified mechanical advantage. In the illustrated embodiment, a high translation and a low force applied by proximal cables 225*a-c* results in a lower translation and a higher force applied to distal cables 125*a-c*. In another embodiment, for example where first diameter portion 251*a-c* comprises a smaller diameter than second diameter portion 252*a-c*, a low translation and a high force applied by proximal cables 225*a-c* results in a higher translation and a lower force applied to distal cables 125*a-c*.

Pulley assemblies 250*a-c* can independently rotate about axle 257. Brake assemblies 253*a-c* can be configured to lock pulley assemblies 250*a-c*, respectively, about axle 257. Upon locking of pulley assemblies, either simultaneously or sequentially, any or all proximal cables 225*a-c* can be tensioned to cause a relatively constant resultant tension on distal cables 125*a-c*.

Interface 200" can be translated linearly via the translation carriage 255 along linear guide rods, such as guide rods 282 or 411 of FIG. 2, similar to interface 200 translating along guide rods 282 and 411 via the translation of carriage 210 of FIG. 2. Bearing assembly 256 can be configured to attach axle 257 to carriage 255.

In some embodiments, cable interface 200" comprises a sensor 201. Sensor 201 can be constructed and arranged to measure one or more parameters or states of cable interface 200". In some embodiments, sensor 201 is similar to sensor 201 described in FIG. 1 hereabove. Alternatively or additionally, one or more brake assembly 253*a-c* and/or bearing assembly 256 can comprise one or more sensors.

Referring now to FIG. 5A, a schematic view of a system for performing a medical procedure is illustrated, consistent with the present inventive concepts. FIG. 5B illustrates a magnified view of the distal portion of a probe of the system of FIG. 5A. System 10 comprises probe 100 having inner probe 140 and outer probe 120; cable interfaces 270*a* and 270*b*; cable control assembly 300; and first and second linear drive assemblies 400*a* and 400*b*. Probe 100; cable control assembly 300 and linear drive assemblies 400*a* and 400*b* can be configured similar to those described in FIG. 1 hereabove.

Inner probe 140 can comprise a probe of similar construction to probe 140 of FIG. 3. Probe 140 includes links 141, and cable 145, terminating in anchor point 143. Inner probe 140 is configured to be slidingly received by outer probe 120, such as via lumen 124.

Cable interfaces 270*a* and 270*b* can comprise functionality similar to cable interface 200*a* described in FIG. 1 hereabove, however in the illustrated embodiment, cable interfaces 270*a* and 270*b* are positioned at a location between the proximal and distal end of outer probe 120. Additionally or alternatively, cable interfaces 270 can be positioned at a location between the proximal and distal end of inner probe 140. Proximal cables 225 are received from cable control assembly 300 by input 271*a* and 271*b* of cable interface 270*a* and 270*b*, respectively, and distal cable 125 is received by outer probe 120 by output 272*a* and 272*b* of cable interface 270*a* and 270*b*, respectively. Each cable 125 extends from cable interface 270*a*, through channel 122 of each link 121 and terminates at its distal end at anchor point 123.

The position of cable interfaces 270a and 270b can be selected to affect the control of links 121 positioned distally to cable interfaces 270a and 270b. For example, if cable interfaces 270a and 270b are positioned in or near the distal portion of outer probe 120, more precise control of the links positioned distally to cable interfaces 270a and 270b can be achieved.

Proximal 225 cables and distal cables 125 of system 10 can have similar or dissimilar construction. In some embodiments, the proximal and distal cables have a dissimilar property selected from the group consisting of: elasticity; flexibility; pushability; column strength; torqueability; diameter; materials of construction; braiding parameter such as pitch or pick count; and combinations thereof.

Figure 6A:
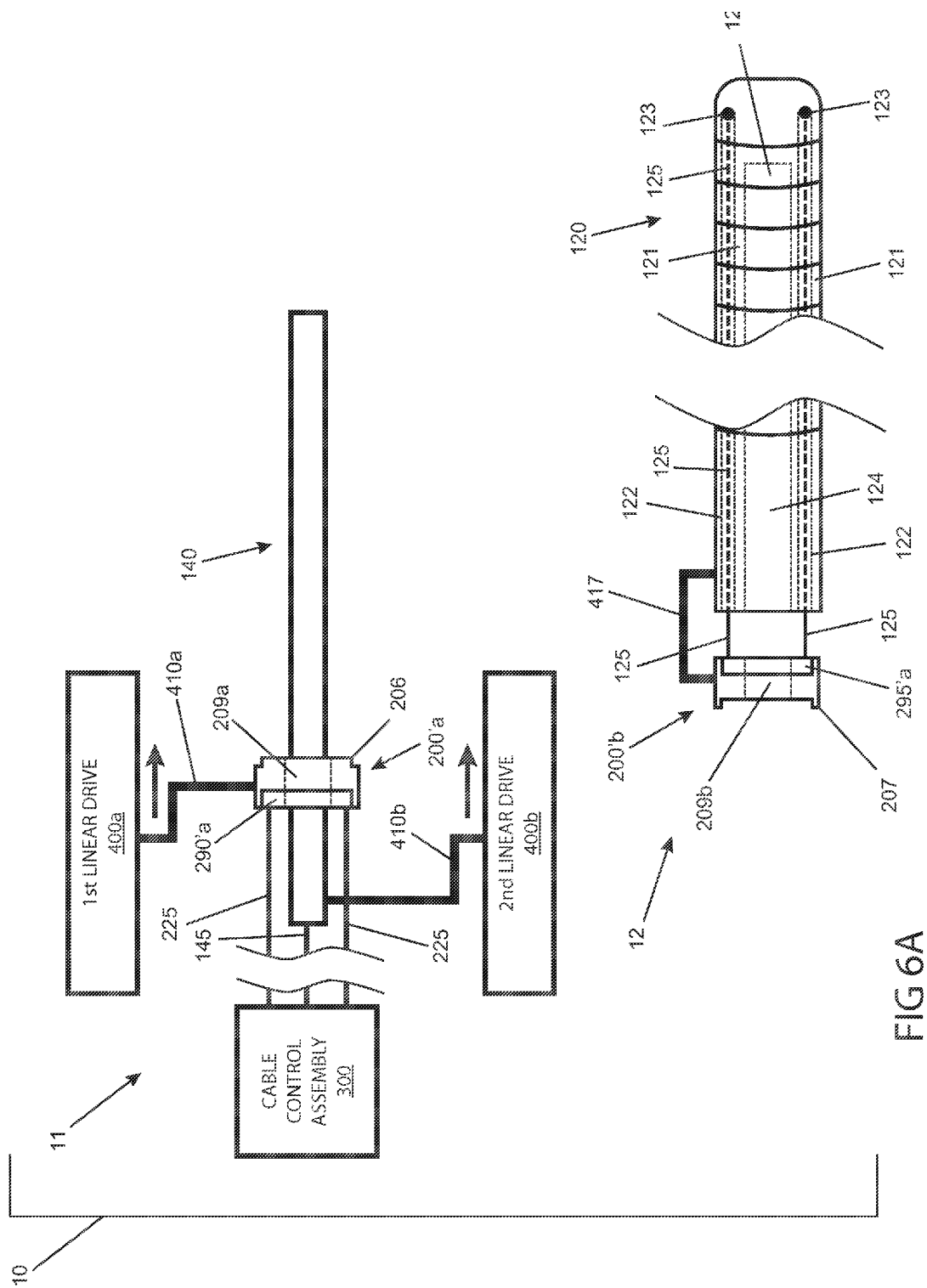
FIG. 6A is a schematic view of a first portion and a second portion of a system for performing a medical procedure, consistent with the present inventive concepts.
Figure 6B:
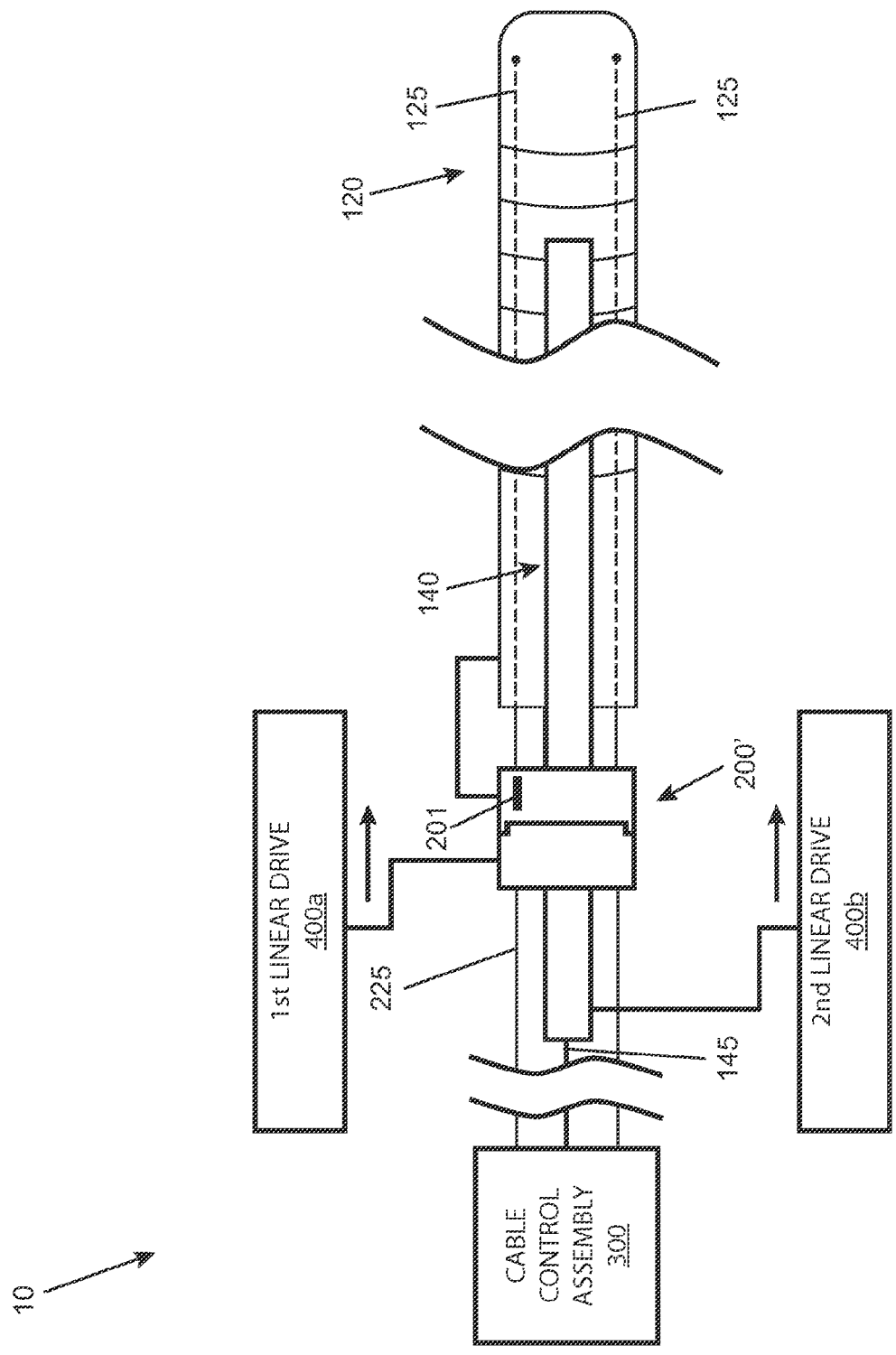
FIG. 6B is a schematic view of a system comprising the first portion and the second portion of FIG. 6A, consistent with the present inventive concepts.

Referring now to FIG. 6A, a schematic view of a first portion and a second portion of a system for performing a medical procedure is illustrated. FIG. 6B illustrates a schematic view of a system comprising the first portion and the second portion of FIG. 6A, consistent with the present inventive concepts. Components of the system illustrated in FIGS. 6A and 6B can be configured similarly to components of system 10 described hereabove. In some embodiments, first portion 11 of system 10 comprises at least cable control assembly 300; first and second linear drive assemblies 400a and 400b; proximal cables 225; inner probe 140; cable 145; and a portion of cable interface 200', portion 200'a. In some embodiments, second portion 12 of system 10 comprises at least outer probe 120; distal cables 125; and a portion of cable interface 200', portion 200'b. Cable interface portion 200'a comprises input 290'a, connector 206, and channel 209a. Cable interface portion 200'b comprises output 295'a, connector 207 and channel 209a. Brace 417 fixedly attaches outer probe 120 to cable interface portion 200'b.

In some embodiments, first portion 11 is re-used as described above in FIG. 1, and/or it can otherwise be used more times than second portion 12 is used, such as when each first portion 11 is used with multiple second portions 12 such as multiple portions that are disposed of after each medical procedure.

As shown in FIG. 6B, cable interface portions 200'a and 200'b can be fixedly attached via connectors 206 and 207, respectively, to form cable interface 200', similar to cable interface 200, 200'', 200a and/or 200b described herein. Channels 209a and 209b align such as to slidingly receive a portion of inner probe 140. Lumen 124 is configured to slidingly receive a portion of inner probe 140, as described herein.

In some embodiments, cable interface 200' comprises a sensor 201. Sensor 201 can be constructed and arranged to measure one or more parameters or states of cable interface 200'. In some embodiments, sensor 201 is similar to sensor 201 described in FIG. 1 hereabove.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the inventive concepts that are obvious to those of skill in the art are intended to be within the scope of the claims. In addition, where this application has listed the steps of a method or procedure in a specific order, it can be possible, and even expedient in certain circumstances, to change the order in which some steps are performed, and it is intended that the particular steps of the method or procedure claim set forth herebelow not be construed as being order-specific unless such order specificity is expressly stated in the claim.

We claim:

1. A system for performing a medical procedure comprising:
    a first multi-linked mechanism comprising a plurality of first links, a proximal end, a distal end and a lumen therethrough; wherein the first multi-linked mechanism is constructed and arranged to transition from a limp state to a rigid state;
    a second multi-linked mechanism comprising a plurality of second links, wherein the second multi-linked mechanism is constructed and arranged to be slidingly received by the lumen of the first multi-linked mechanism and to transition from a limp state to a rigid state;
    a set of proximal cables comprising at least a first proximal cable and a second proximal cable;
    a set of distal cables comprising at least a first distal cable and a second distal cable;
    a cable control assembly constructed and arranged to independently apply tension to the first proximal cable and the second proximal cable; and
    a cable interface assembly constructed and arranged to receive a force from at least the first proximal cable and the second proximal cable and to transmit a corresponding force to at least the first distal cable and the second distal cable;
    wherein the force applied to the first distal cable and the second distal cable steers at least one of the first multi-linked mechanism or the second multi-linked mechanism;
    wherein the cable interface assembly comprises at least one gimbal, wherein the at least one gimbal comprises an input surface that attaches to the set of proximal cables and an opposing output surface that attaches to the set of distal cables.

2. The system of claim 1, wherein the system comprises a first portion and a second portion and wherein at least the first portion is constructed and arranged to be used in multiple medical procedures.

3. The system of claim 2, wherein the first portion comprises at least one of: an input portion of the cable interface assembly; the set of proximal cables; a user interface of the system; the cable control assembly; a pulley of the system; a linear drive of the system; or the second multi-linked mechanism.

4. The system of claim 2, wherein the system further comprises a second portion constructed and arranged to be used in fewer medical procedures than the first portion.

5. The system of claim 4, wherein the second portion comprises at least one of: an output portion of the cable interface assembly; the set of distal cables; a pulley of the system; or the first multi-linked mechanism.

6. The system of claim 1, wherein the cable interface assembly comprises a first portion and a second portion, wherein the first portion is constructed and arranged to be used in more medical procedures than the first portion.

7. The system of claim 6, wherein the first portion comprises an input constructed and arranged to attach to the set of proximal cables and the second portion comprises an output constructed and arranged to attach to the set of distal cables.

8. The system of claim 6, wherein the second portion is constructed and arranged to be used in a single medical procedure.

9. The system of claim 1, wherein the cable interface assembly comprises an input constructed and arranged to attach to the set of proximal cables and an output constructed and arranged to attach to the set of distal cables.

10. The system of claim 1, wherein the cable interface assembly is constructed and arranged to transmit a first force to the first distal cable and a second force to the second distal cable simultaneously.

11. The system of claim 1, wherein the cable interface assembly is constructed and arranged to transmit a first force to the first distal cable and a second force to the second distal cable sequentially.

12. The system of claim 1, wherein the cable interface assembly is constructed and arranged to provide a mechanical advantage between the proximal cables and the distal cables.

13. The system of claim 1 wherein the at least one gimbal comprises at least two gimbals.

14. The system of claim 13 wherein the at least two gimbals comprises a first gimbal that rotates about a first axis and a second gimbal that rotates about a second axis oriented relatively 90° to the first axis.

15. The system of claim 1, wherein the cable interface assembly is constructed and arranged to amplify translation between the first proximal cable and the first distal cable.

16. The system of claim 1, wherein the cable interface assembly is constructed and arranged to amplify force applied between the first proximal cable and the first distal cable.

17. The system of claim 1, further comprising a second cable interface assembly constructed and arranged to receive a force from at least one cable and transmit a force to at least one cable.

18. The system of claim 1, wherein the distal cables are constructed and arranged to steer the first multi-linked mechanism.

19. The system of claim 1, wherein the distal cables are constructed and arranged to steer the second multi-linked mechanism.

20. The system of claim 1, wherein the set of proximal cables are operably attached to the cable interface assembly in a first pattern and the set of distal cables are operably attached to the cable interface assembly in a second pattern.

21. The system of claim 1, wherein the set of proximal cables comprise a first quantity and the set of distal cables comprise a second quantity similar to the first quantity.

22. The system of claim 1, further comprising at least one linear drive.

23. The system of claim 22 wherein the at least one linear drive is attached to the first multi-linked mechanism and the cable interface assembly.

24. The system of claim 23 further comprising a second cable interface assembly and a second linear drive attached to the second multi-linked mechanism and the second cable interface assembly.

25. The system of claim 22 wherein the at least one linear drive is attached to the second multi-linked mechanism and the cable interface assembly.

26. The system of claim 1, further comprising a linear compensator constructed and arranged to allow motion between the cable interface assembly and at least one of the first multi-linked mechanism and the second multi-linked mechanism.

27. The system of claim 1, further comprising a sensor constructed and arranged to measure a parameter of the cable interface assembly.

28. The system of claim 27 wherein the sensor is constructed and arranged to quantify a parameter of the cable interface assembly selected from the group consisting of: an amplification of proximal to distal cable translation; an amplification of proximal to distal cable tension; angular rotation of a component of the cable interface assembly such as a rotating gimbal or a rotating pulley; a linear displacement of a component of the cable interface assembly; a linear displacement of a proximal cable; a linear displacement of a distal cable; tension in a proximal cable; tension in a distal cable; and combinations thereof.

29. The system of claim 1, wherein the first multi-linked mechanism further comprises at least one sideport.

30. The system of claim 1, wherein the first multi-linked mechanism further comprises at least two channels each constructed and arranged to slidingly receive one of the first or second distal cables.

31. The system of claim 1, wherein the set of distal cables further comprises a third distal cable, wherein the first multi-linked mechanism comprises at least three channels each constructed and arranged to slidingly receive one of the first, second, or third distal cables.

32. The system of claim 1, further comprising at least one working channel between the first multi-linked mechanism and the second multi-linked mechanism.

33. The system of claim 1, further comprising a tool with a flexible distal portion.

* * * * *

UNITED STATES PATENT AND TRADEMARK OFFICE
CERTIFICATE OF CORRECTION

PATENT NO.         : 9,913,695 B2
APPLICATION NO.    : 14/888189
DATED              : March 13, 2018
INVENTOR(S)        : Gabriel Johnston et al.

It is certified that error appears in the above-identified patent and that said Letters Patent is hereby corrected as shown below:

In the Claims

Claim 6, Column 18, Line 57, please delete "first" and add ---second--- after "medical procedures than the"

Signed and Sealed this
Twenty-sixth Day of June, 2018

Andrei Iancu
*Director of the United States Patent and Trademark Office*